United States Patent [19]
Deaton et al.

[11] 3,945,392
[45] Mar. 23, 1976

[54] DISPOSABLE SAFETY FLOAT VALVE

[75] Inventors: David W. Deaton; Stephen M. Brower, both of Dallas; Marshall P. Durham Jr., Desota, all of Tex.

[73] Assignee: C. R. Bard, Inc., Murray Hill, N.J.

[22] Filed: Oct. 10, 1974

[21] Appl. No.: 513,597

Related U.S. Application Data

[62] Division of Ser. No. 279,062, Aug. 9, 1972, Pat. No. 3,848,628.

[52] U.S. Cl. ............ 137/205; 137/202; 137/451; 137/434; 128/277
[51] Int. Cl.² ........................................ A61M 1/00
[58] Field of Search .......... 137/205, 202, 451, 434; 128/276, 277; 220/306

[56] References Cited
UNITED STATES PATENTS

| | | |
|---|---|---|
| 2,999,500 | 9/1961 | Shurer .............................. 128/276 |
| 3,429,313 | 2/1969 | Romanelli ......................... 128/276 |
| 3,519,163 | 7/1970 | Bardell ............................. 220/306 |
| 3,699,815 | 10/1972 | Holbrook ........................ 128/276 X |
| 3,739,976 | 6/1973 | MacDaniel ........................ 220/306 |
| 3,774,613 | 11/1973 | Woods ............................... 128/277 |

*Primary Examiner*—Alan Cohan

[57] ABSTRACT

The specification discloses a medical suction apparatus including a generally rigid container. A pair of conduits extend from the lid of the container for connection to a patient area to be drained and for connection to a vacuum source. In operation, fluid is drawn from the area to be drained and collected within the container. A flexible float valve is connected to the underside of the lid and is operable upon fluid overflow conditions to obstruct the vacuum conduit to prevent fluid from being drawn into the vacuum source.

9 Claims, 29 Drawing Figures

DISPOSABLE SAFETY FLOAT VALVE

RELATED APPLICATIONS

This application is a divisional of Ser. No. 279,062, filed Aug. 9, 1972 now U.S. Pat. No. 3,848,628.

FIELD OF THE INVENTION

This invention relates to a suction collection apparatus having a float valve, and more particularly relates to a float valve for use with a suction apparatus wherein fluids are drawn from a patient area and are stored in a container.

THE PRIOR ART

Suction devices are commonly used in a number of medical applications to draw various fluids from a patient area and to store the fluids for later disposal. For example, suction devices have heretofore been utilized to draw aspirated fluids from a patient during a surgical operation, and during the postoperative period. In addition, suction devices are used to drain fluids from the gastrointestinal tract, as well as to drain pulmonary mucus in tracheal incisions and the like.

Several types of suction devices have been heretofore utilized. For example, rigid glass bottles, disposable plastic containers and rigid plastic containers having disposable flexible sacks have been heretofore used to receive fluid drained from a patient. All of these prior fluid collection devices have generally included a container for collecting the fluid, along with a lid having a vacuum inlet and a fluid inlet. In such devices, care must be taken not to allow fluid being collected within the container to overflow into the vacuum inlet, as the fluid could severely contaminate the hospital vacuum system. Thus, valves have heretofore been developed to prevent such overflow from passing into the vacuum system. However, such prior overflow-prevention valves have generally been relatively expensive to manufacture and have often been so complex in construction that proper operation over a long period of time could not be assured. In addition, once a fluid overflow occurs with many prior valves, the valves are difficult to clean or replace.

SUMMARY OF THE INVENTION

In accordance with the present invention, a float valve is provided which substantially eliminates or reduces the problems of the prior art devices. The valve includes a flexible member having one end portion connectable to the underside of a suction collection lid and further having an unconnected free end. The valve member is sufficiently flexible that the free end hangs downwardly out of contact with the vacuum inlet in the lid when the fluid level within the collection container is below a predetermined level. When the fluid rises above the predetermined level, the valve member floats on the level of the fluid until the valve member obstructs the vacuum inlet to prevent the fluid from being sucked into the vacuum inlet.

DESCRIPTION OF THE DRAWINGS

For a more complete understanding of the present invention and for further objects and advantages thereof, reference is now made to the following description, taken in conjunction with the accompanying drawings, in which.

DESCRIPTION OF THE PREFERRED EMBODIMENTS

Figure 1:
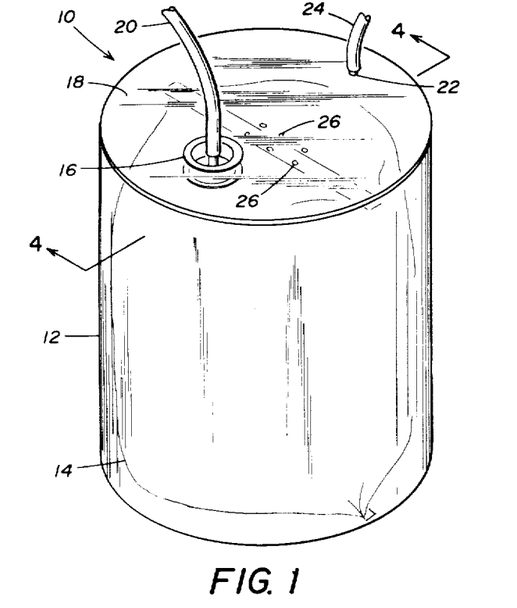
FIG. 1 illustrates a perspective view of an embodiment of the invention.

FIGS. 1-5 illustrate an embodiment of the invention. Referring to FIG. 1, a medical suction apparatus 10 comprises a generally rigid container 12 which is preferably an open-topped transparent plastic cylinder. Container 12 will generally include volume indicating markings, not shown, in order to enable visual reading of the fluid level stored in the container. A flexible drainage bag 14 is supported within the container 12 by a conduit member or port device 16 attached within a cover or lid 18 for the container. Cover 18 preferably comprises a transparent plastic lid which is snapped into place over the open top of the container 12 to tightly seal the container for maintenance of dependable suction during operation of the device. A flexible hose or tube 20 is connected at one end to the conduit member 16 and extends to a patient area for receiving fluids. A vacuum conduit member 22 extends through the cover 18 and is connected to a flexible tube 24 which extends to a source of reduced pressure. The source of reduced pressure may comprise any suitable source of vacuum or suction which is commonly found in hospitals. The conduit member 22 may comprise a plastic port integrally formed with the cover 18, or alternatively may comprise a metal tube which is threadedly received in an aperture in the cover 18.

An alternate embodiment of the present device, not shown, may comprise a second conduit member communicating with bag 14 through the cover 18. A short tube may be connected to the second conduit member and the tube normally clamped shut. After filling of the bag 14 with liquid, the tube may be unclamped and the liquid poured out through the second conduit member and the short tube. The short tube may then be clamped and the suction operation continued.

Apertures 26 are spaced along the upper portion of the flexible bag 14 in the area between the conduit members 16 and 22. Preferably, the combined surface area of the apertures 26 is greater than the surface area of the central opening of conduit member 22, and the geometry and location of the apertures 26 are such that the resistance to gas flow therethrough is slightly less than the resistance to gas flow through conduit member 22. In this case, bag 14 will remain in a limp unstressed condition during initial operation of the device, and will gradually become opened as it is filled with liquid.

In some cases, it may be desirable to put a very slight initial stress on bag 14 prior to filling with liquid. For example, if bag 14 were supported from cover 18 in a different manner than as shown, it may be desirable to insure that the bag 14 is fully opened prior to filling with fluid. In such instances, the apertures 26 may be dimensioned and positioned in the bag 14 such that the resistance to gas flow therethrough is equal to or slightly greater than the resistance to gas flow through the conduit member 22. By thus controlling the ratio of gas flow resistance of apertures 26 and conduit member 22, the pressure gradient across bag 14 may be controlled to impart a selected amount of slight stress to bag 14. Upon the application of vacuum to the device in this case, bag 14 will slowly become distended in order to receive fluid. However, the apertures 26 will be dimensioned such that bag 14 will not be stressed by an amount sufficient to cause rupture or other damage.

In operation of the apparatus shown in FIG. 1, vacuum or suction is applied via the tube 24 through the conduit member 22 to the space between the flexible bag 14 and the generally rigid container 12. The suction is communicated through the apertures 26 into the interior of the bag 14, and is then directed through the conduit member 16 and the tube 20 to the patient area. Fluid from the patient area is drawn by the suction through the tube 20 and the conduit member 16 to the bag 14 which receives and stores the fluid. Because of the location of the apertures 26 in the upper portion of the bag 14, no fluid escapes into the interior of the container 12.

The application of reduced pressure to the area between the bag 14 and the container 12 insures that the bag 14 does not close up or collapse during suction operation. However, because of the construction of the present invention, the pressure on the exterior and interior of the bag 14 is equalized, and thus the bag 14 is not outwardly stressed, but instead remains in a relaxed unstressed condition during suction operation. Elimination of outward stress on the bag enables the use of a relatively lightweight and inexpensive material for the construction of the bag, without danger of rupture of the bag. After the bag is filled with liquid, application of vacuum or suction through the tube 24 is terminated, the cover 18 is removed and the bag 14 is then removed, emptied and disposed of. Although not shown, a normally closed port may be defined in the bag to enable the bag to be easily emptied when desired. A new sterile bag 14 is then connected to the cover 18 and inserted into the rigid container 12 for reception of additional fluid, without the necessity of any sterilization or cleaning of the container 12.

Figure 2:
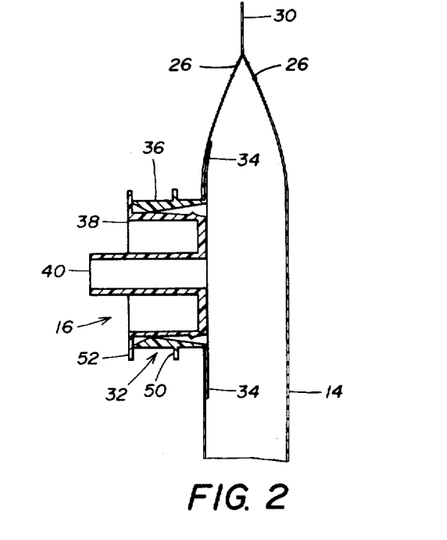
FIG. 2 is a sectional view taken along the upper portion of the flexible bag shown in FIG. 1 prior to connection within the rigid outer container.
Figure 3:
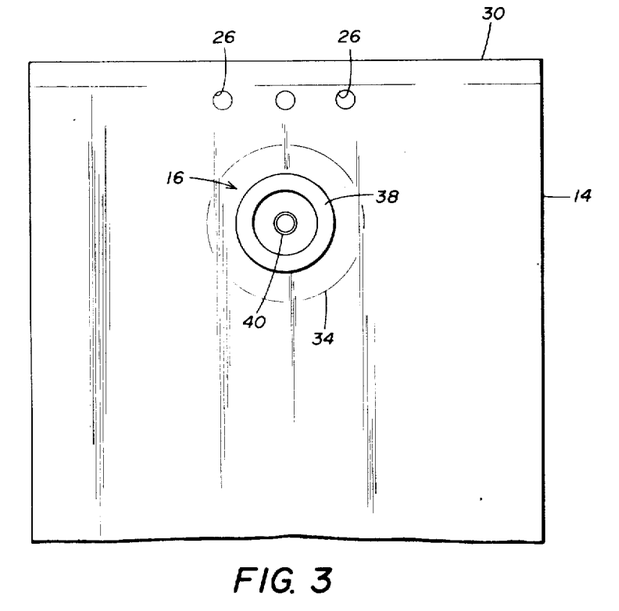
FIG. 3 is a side view of the upper portion of the flexible bag shown in FIG. 1.

FIGS. 2 and 3 illustrate in greater detail the construction of the flexible bag 14. Bag 14 preferably comprises a generally flat, rectangular bag sealed around the peripheral edges and sealed at the top by a heat-sealed strip 30. The conduit member 16 is mounted through a hole in one side of the bag 14 and comprises a first conduit member 32 having an annular base 34 which is heat-sealed or glued to the interior of the bag 14. The first conduit member 16 also includes a hollow cylindrical extension 36 which extends from base 34 through the hole in the bag 14. The cylindrical extension 36 includes an inwardly extending area of increased thickness to provide a friction fit with a second conduit member 38. The second conduit member 38 includes a central tube portion 40 having an opening therethrough to provide a path to the interior of the bag 14. Prior to attachment of the bag 14 to the cover 18, the conduit member 16 extends from the side of the bag in the manner shown in FIG. 2. The bag 14 may thus be rolled into a relatively compact shape for easy packaging and storage.

Figure 4:
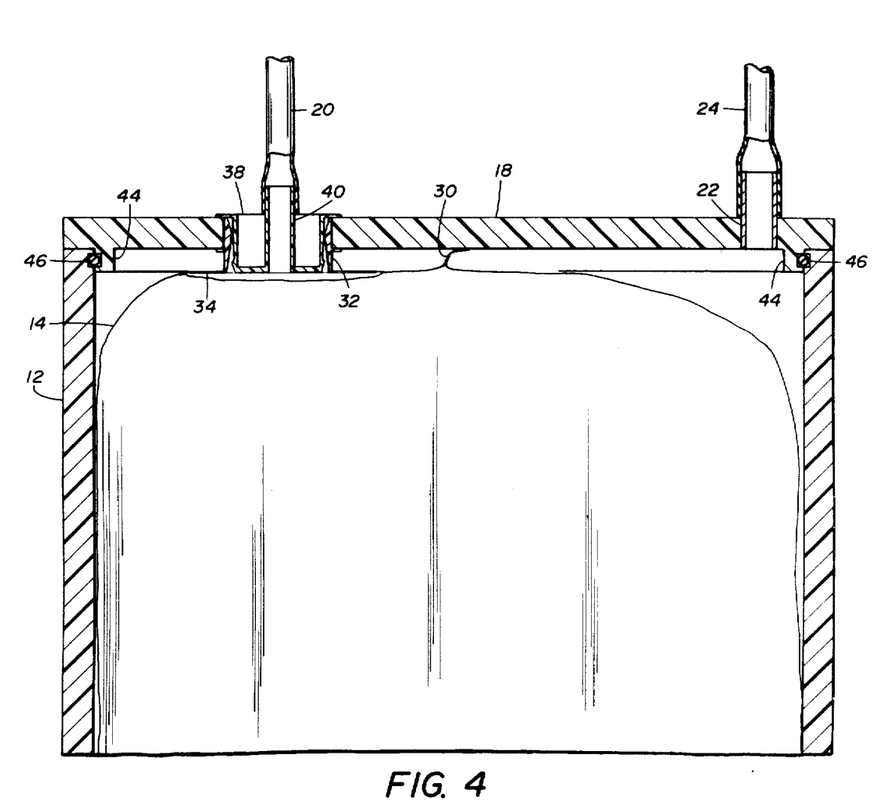
FIG. 4 is a sectional view of the upper part of the assembled invention taken generally along the section line 4—4 in FIG. 1 illustrating the outer rigid container and the flexible bag.

FIG. 4 illustrates in greater detail the support of the bag 14 within the container 12. The first conduit member 32 extends through an aperture in the cover 18 and frictionally receives the second conduit member 38 in order to secure the bag to the cover 18. The drainage tube 20 is then secured to the central tube portion 40 and is extended to the patient area to receive fluid. The cover 18 includes an annular extension 44 which is dimensioned to be securely received by the interior side walls of container 12. An O-ring 46 is carried by the extension 44 to ensure a vacuum tight seal. The conduit 22 extends through the cover 18 and is rigidly connected thereto in order to receive the vacuum tube 24 in the manner previously described.

Figure 5:
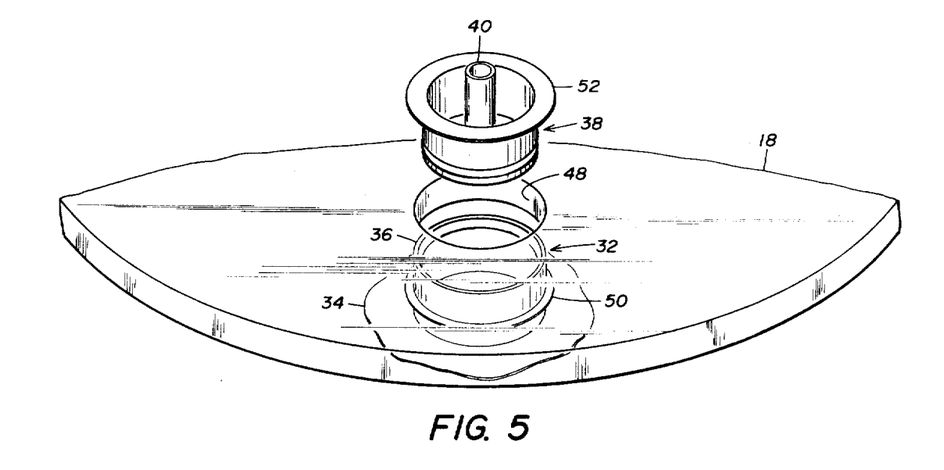
FIG. 5 is an exploded view illustrating the connection of the drainage conduit member of FIG. 1.

FIG. 5 illustrates an exploded view illustrating the manner of connection of the first conduit member 32 and the second member 38 to the cover 18. Bag 14 is omitted from FIG. 5 for ease of illustration. The first conduit member 32 is extended through a hole 48 formed in the cover 18. An annular lip 50 on the cylindrical extension 36 abuts with the lower edge of the hole 48 to properly position the first conduit member 32. The second conduit member 38 is then disposed through the hole 48 from the top of cover 18 and manually snapped into frictional fit inside the cylindrical extension 36. An annular lip 52 formed on the conduit member 38 properly positions the conduit member 38 relative to the cover 18. The drainage tube 20 is then connected to the tube portion 40, wherein fluids from the patient area may be directed into the interior of the bag 14. The above-described conduit member construction enables ease of attachment of the bag 14 to the cover 18, while maintaining a vacuum tight connection. However, due to the provision of apertures 26 in bag 14, vacuum leaks in the conduit members or in the cover do not cause the bag 14 to collapse, as is the case with some prior art devices.

Figure 6:
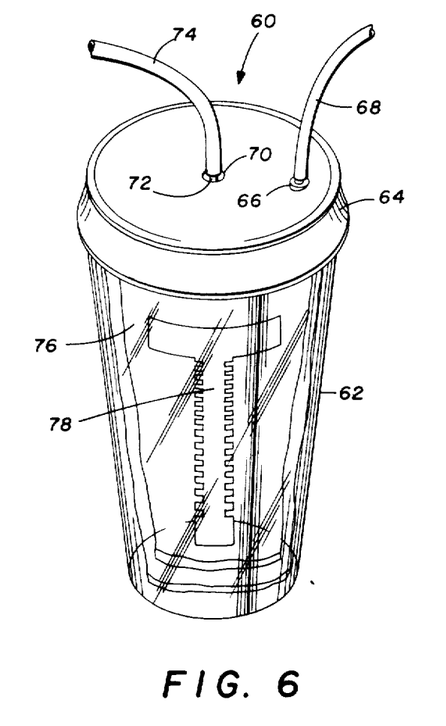
FIG. 6 is a perspective illustration of another embodiment of the invention.

FIG. 6 illustrates a medical suction apparatus 60 which includes a number of improvements over the device shown in FIGS. 1–5 and which is the preferred embodiment of the present invention. Suction apparatus 60 comprises an open top container or canister 62 and a lid 64. Lid 64 includes a vacuum inlet 66 to which may be attached a flexible tube 68 which leads to a source of reduced pressure. Lid 64 also includes a fluid inlet port 70 through which extends a fluid inlet conduit 72. A rubber hose 74 may be attached to the conduit 72 and extended to a patient area in order to draw fluid from the patient. A double walled bag or sack 76 is connected to the fluid inlet conduit in a manner to be subsequently described and is disposed within the container 62 in order to receive the fluid drained from the patient area. Sack 76 preferably includes indicia 78 printed thereon in order to enable measurement of the amount of fluid contained within the sack.

Figure 7:
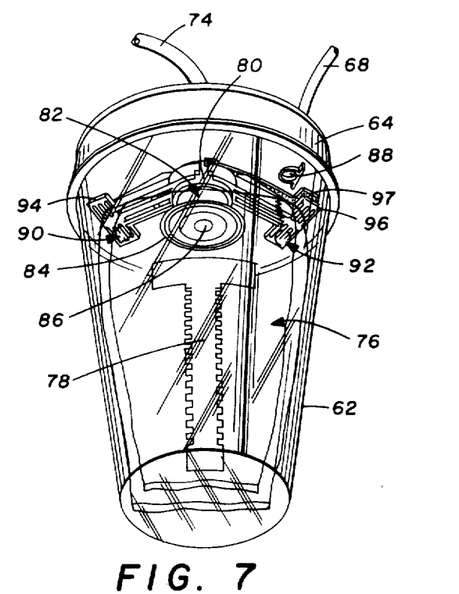
FIG. 7 is a perspective view of the underside of the container assembly shown in FIG. 6.

FIG. 7 illustrates the underside of the container 62 and lid 64. As will be described later in greater detail, the underside of lid 64 includes a downwardly extending annular projection 80 through which the fluid inlet port 70 extends. The upper portion of the sack 76 includes a resilient fluid inlet conduit member or port device 82. Preferably, the port device 82 is constructed of plastic and is shaped to be frictionally fit over the annular projection 80 in order to support the sack 76 within the container 62 in the manner illustrated. The port device 82 is bonded to the top of the sack 76 by means of an annular heat seal 84. The port device 82 includes a fluid inlet conduit 86 which communicated with conduit 72 in order to admit fluid received from the hose 74 into the interior of the sack 76.

A vacuum inlet port 88 extends through the lid 64 for communication with the vacuum inlet 66 and the hose 68 in order to admit a partial vacuum to the space between the exterior of the sack 76 and the container 62. Apertures 90 and 92, to be later described in detail, are formed through the sidewalls of the sack 76 in order to tend to equalize the pressure between the interior and the exterior of the sack 76 to prevent collapse thereof upon application of vacuum.

An important aspect of the present invention is the provision of a pair of sack separator levers 94 and 96. Levers 94 and 96 are pivoted to the underside of the lid 64 and include end portions which are disposed between the underside of the lid 64 and the port device 82 of the sack 76. As will be subsequently described, when the sack 76 is full of fluid, the levers 94 and 96 may be manually pivoted in order to separate the sack 76 from the lid 64 to enable disposal of the sack 76. A float valve 97 is mounted to the underside of the lid 64 above the sack separator 96. In a manner to be subsequently described, the float valve 97 prevents passage of liquid through the vacuum inlet 88 upon overflow of fluid within the container 62.

Figure 8:
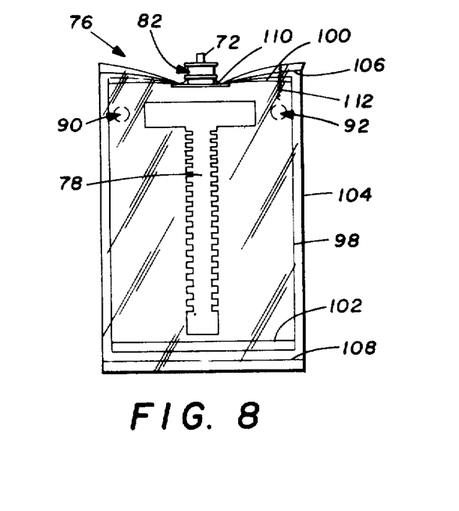
FIG. 8 is a side view of the disposable sack constructed in accordance with the invention.

FIG. 8 is a side view of the rectangular sack 76. Preferably, the sack 76 is constructed from a suitable transparent flexible plastic such as polyethylene modified with ethyl vinyl acetate. Sack 76 includes an inner flat sack 98 constructed by an upper heat seal 100 and a lower heat seal 102 made on a section of plastic flat bag stock. The inner sack is disposed within an outer sack 104 which is constructed of the same transparent plastic material. The outer sack 104 is also constructed from conventional flat bag stock and includes an upper heat seal 106 and a lower heat seal 108. The port device 82 comprises a two piece member constructed in a similar manner as the conduit member 16 shown in FIG. 2. The port device 82 is heat sealed by a circular heat seal 110 through the tops of the bags 98 and 104.

In the preferred embodiment, a line of perforations 112 is defined in one upper end portion of the sack 76. After the sack is filled with fluid, the nurse or other operator may grasp the corner of the sack and tear the corner of the sack along the perforations 112. The fluid within the sack may then be quickly dispensed from the sack.

The aperture 90 is formed through the side wall of the outer sack 104, while the aperture 92 is formed through the side wall of the inner sack 98. In the preferred embodiment, a pair of apertures 90 are formed through the front and back of sack 104 by a punch operation, while a similar pair of apertures 92 are formed through the front and back of sack 98. The apertures 90 and 92 are spaced apart in this manner to provide a splash guard function for the system. When fluid is introduced into the sack 76, fluid tends to splash and form an aerosol type medium which tends to exit through a conventional open aperture. By the spacing of the apertures 90 and 92 in the manner illustrated, the apertures act as a baffle to aerosol to prevent leakage within the container 62. The provision of the double sack shown in FIG. 8 ensures the integrity of the bag and substantially reduces the possibility of a fluid leak. In addition, in case of overflow of the inner bag 98, the outer bag 104 would serve as an auxiliary collection receptacle.

In construction of the sack 76, two different sizes of flat bag stock are utilized. Suitable lengths are cut from the two different sizes of bag stock and indicia 78 is printed upon the smallest size bag stock. Additional indicia may be printed upon the larger bag stock, if desired. The upper ends of each of the bag portions are then heat sealed to form sacks 98 and 104. A circular hole is then punched into the top of each of the sacks and the inner sack 98 is then inserted through the bottom of the outer sack 104. The port device 82 is inserted through the circular hole and the circular heat seal 110 is made to firmly connect the port device 82 to both of the sacks 98 and 104. The lower open end of the sack 104 is then peeled back and the heat seal 102 is made along the bottom of the inner sack 98. The heat seal 108 is then made on the bottom of the sack 104 in order to form the complete sack 76.

Figure 9:
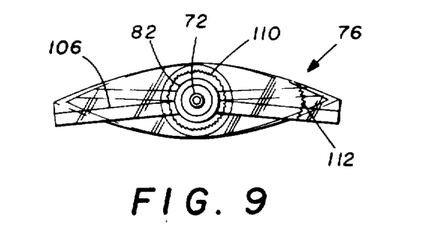
FIG. 9 is a top view of the sack shown in FIG. 8.

FIG. 9 is a top view of a folded sack 76. In this folded configuration, the sack 76 may be easily packaged in a small plastic bag to maintain the sack 76 in a sanitary condition during transportation and storage. FIG. 9 also illustrates in greater detail the annular heat seal 110 which bonds the port device 82 to the top of the sacks 98 and 104.

Figure 10:
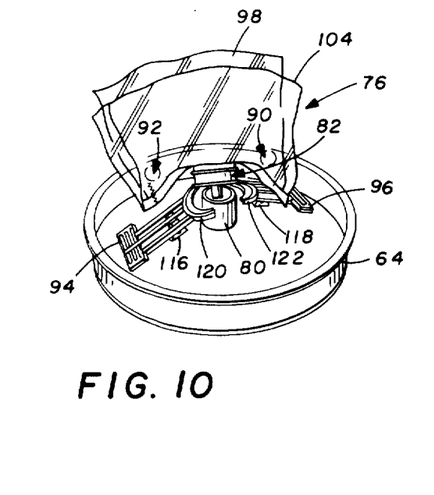
FIG. 10 is a perspective view illustrating the initial attachment of the disposable sack to the underside of the lid of the present container.

FIG. 10 illustrates connection of the sack 76 to the underside of the lid 64. The lid 64 is placed in an upsidedown position and the port device 82 is placed on the top of the annular projection 80. The thumbs of the operator are then used to push the port device 82 down over the projection 80. The port device 82 is preferably constructed from a resilient plastic material such as polyethylene or the like and is dimensioned to tightly receive the projection 80. As shown in FIG. 10, the sack separator levers 94 and 96 are pivotally connected to the underside of a lid 64 by means of pivots 116 and 118. As the port device 82 is pushed over the projection 80, the levers 94 and 96 are pivoted such that the semicircular end portions 120 and 122 of the levers are disposed between the underside of the lid 64, the sack is disposed within the container 62 and the lid 64 is placed on the top of container 62. Suction is applied to hose 68 and causes the lid 64 to be snapped into place on the top of the container 62. Fluid may then be drawn from a patient area through the hose 74 into the sack 76.

Figure 11:
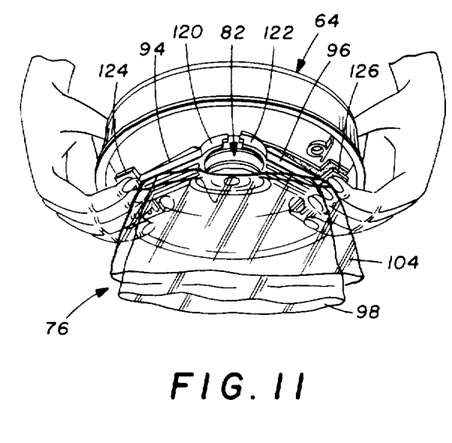
FIG. 11 illustrates the separation of the disposable sack from the lid of the invention.

FIG. 11 illustrates the disengagement of the sack 76 from the lid 64 after the sack 76 is filled with fluid. Generally, the nurse or other operator of the suction system will remove the lid 64 from the container 62 and carry the fluid-filled sack to a sink or other disposal location. The nurse will then place her thumbs on the top of the lid 64 and place the ends of her fingers on pads 124 and 126 which are integral end portions of the levers 94 and 96, respectively. The nurse then pulls the pads 124 and 126 toward the underside of the lid 64 and the curved end portions 120 and 122 push the port device 82 off the annular projection 80. The fluid-filled sack 76 is separated from the lid 64 and a new sack may be attached to the lid 64 and additional fluid collected.

Figure 12:
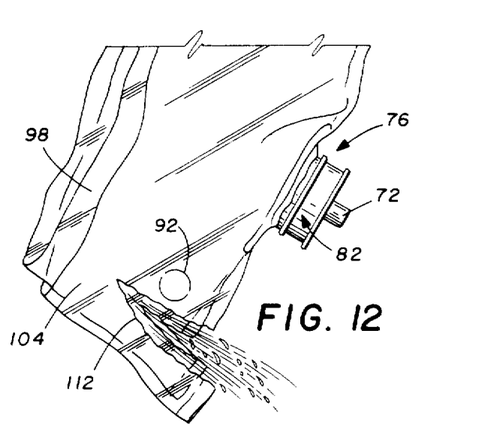
FIG. 12 illustrates the emptying of liquids from the disposable sack of the invention.

FIG. 12 illustrates the tearing of the corner of the sack 76 along the line of perforations 112. This opens the upper corner of both the outer sack 104 and the inner sack 98 and enables the fluid contained within the sack 76 to be quickly poured into a sink or other suitable receptacle. The sack 76 may then be disposed of in the trash or the like. In the preferred embodiment, it has been found desirable to pour out the contents of fluid of the sack 76 prior to disposal of the sack in order to prevent subsequent contamination of personnel which are required to handle the sack during incineration or other disposal.

Figure 13:
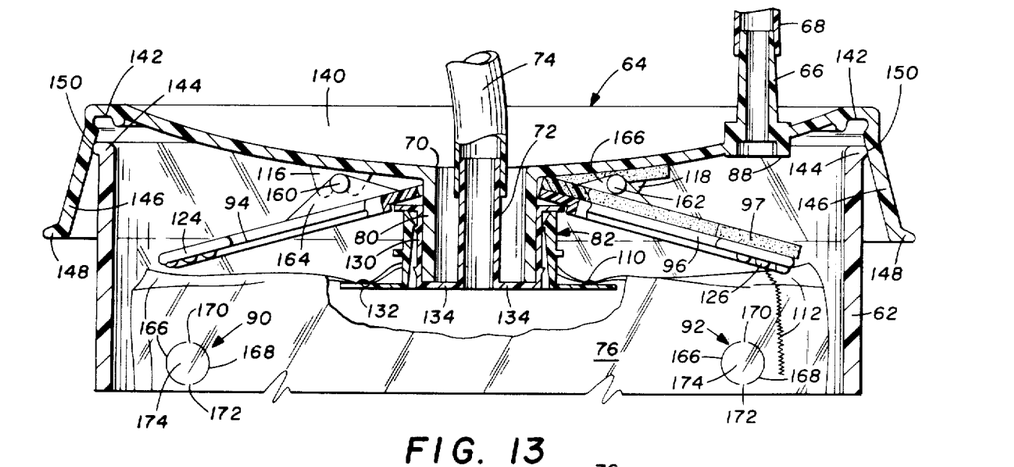
FIG. 13 is a sectional view through the upper portion of the present container during attachment of the lid to the container.

FIG. 13 illustrates a partially sectioned view of the present assembly during the attachment of the sack-bearing lid 64 to the container 62. In FIG. 13, sack 76 has been attached to the underside of lid 64 by forcing the port device 82 over the annular projection 80 in the manner previously described. As shown in FIG. 13, the port device 82 comprises two interlocking plastic pieces 130 and 132. An important aspect of the invention is that piece 134 includes an annular diaphragm which supports in the center thereof the fluid inlet conduit 72. The diaphragm 134 is constructed to be responsive to the magnitude of vacuum applied to the interior of the container 62. The greater the vacuum applied, the more the diaphragm 134 is flexed to cause the sidewalls of piece 130 to more tightly grip the outer walls of the annular projection 80. This prevents the port device 82 from being sucked off from the annular projection 80 upon the application of high vacuum.

As shown in FIG. 13, the lid 64 includes a downwardly directed concavo-convex top portion 140 having in the center thereof the fluid inlet port 70 which extends through the projection 80. The particular downwardly directed concavo-convex construction of the top 140 provides great strength to the top and enables the top to be integrally constructed from injection molded plastic such as nylon or the like. The vacuum inlet 66 is integrally formed from the lid and extends upwardly to enable connection of a hose 58 thereto.

An annular groove 142 is formed about the underside periphery of the lid 64, with the groove being shaped with a bead 144 which extends about the upper lid of the container 62. A downwardly extending outwardly flared side 146 integrally extends below the groove 142. The side 146 includes an annularly outwardly directed flange 148 to enable ease of handling of the lid.

Figure 14:
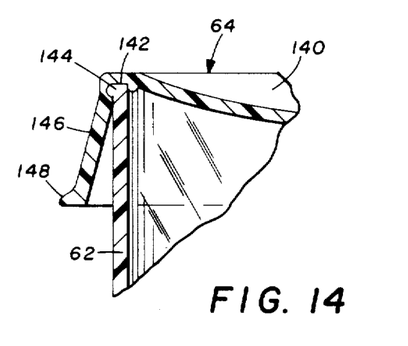
FIG. 14 is a sectional view, partially broken away, showing the final vacuum tight connection of the lid with the container.

An important aspect of the present lid is that a transient seal portion 150 is provided on the interior of the side 146. As shown in FIG. 13, when the lid 64 is initially set upon the top of the container 62, the bead 144 abuts the transient sealing portion 150 of the side 146. Vacuum is applied through the hose 68 and through the vacuum port 88 into the container 62. If the hose 74 is then temporarily obstructed by the nurse or operator, sufficient suction is applied to the lid 64 in order to move the lid 64 downwardly such that the bead 144 snaps into place into the groove 142. The mating of the bead 144 within the groove 142 is illustrated in FIG. 14. As the lid 64 is pulled downwardly into seating engagement with the container 62, the sidewall 146 is slightly cammed outwardly until the bead 144 snaps into place into the groove 142. A vacuum fit is then provided at the juncture of the bead 144 and the groove 142. No O-ring is required for the lid 64. The lid 64 is preferably constructed from a flexible plastic such as nylon or the like to enable the outward bending of the side 146 during attachment of the lid 64 to the container 62. Similarly, the edge 146 may be outwardly bent by the hands of a nurse in order to enable easy removal of the lid 64.

FIG. 13 also illustrates in detail the pivotal connection of the levers 94 and 96 to the underside of the lid 64. Pivots 116 and 118 are integrally formed on the underside of the lid 64 and include openings therein for receiving cylindrical pivot members 160 and 162. Pivot member 160 is carried by a flange 164 integrally formed with lever 94, while pivot member 162 is carried by a flange 166 integrally formed to the lever 96. The pads 124 and 126 of the levers are provided with corrugations in order to improve the strength of the levers. As previously noted, upon manual depression of the pads 124 and 126, the levers 94 and 96 may be pivoted in order to remove the port device 82 from the annular projection 80.

FIG. 13 also illustrates the attachment of the float valve 97 between the lever 96 and the underside of the lid 64. In the normal position, the float valve 97 hangs downwardly out of contact with the vacuum inlet 88. During an overflow condition, as will be subsequently described, the float valve 97 floats on the surface of the fluid in order to obstruct the opening of the vacuum inlet 88 to prevent fluid from being drawn therethrough.

FIG. 13 also illustrates in greater detail the construction of the apertures 90 and 92 formed through the sack 76. Each of the apertures are formed by a pair of semicircular slits 166 and 168. Under low vacuum conditions, air is drawn through the slits 166 and 168 in order to equalize the pressure between the interior and exterior of the sack 76. The slits 166 and 168 define small spaced apart hinge portions 170 and 172 of plastic material which support a valve flap 174 of flexible plastic. In low vacuum conditions, the flap 174 substantially obstructs the apertures 90 and 92 except for the small openings provided by the slits 166 and 168.

However, upon the application of greater vacuum, the edges of the flaps 174 tend to be bent to provide a larger effective opening for the apertures 90 and 92. The flaps 174 thus tend to act as a butterfly type valve in order to provide sufficient resistance to flow through the apertures so that the sack 76 will fully expand under low vacuum. However, upon the application of high vacuum and resulting high air flow through the apertures, the flaps 174 are bent to provide an enlarged flow opening to eliminate the possibility of rupture of the sack at a weak point. Additionally, as previously noted, aperture 90 is formed in an outer sack 104, while the aperture 92 is formed in an inner sack 98 to provide a splash baffle to prevent leakage of medical fluid into the interior of the container 62.

Figure 15:
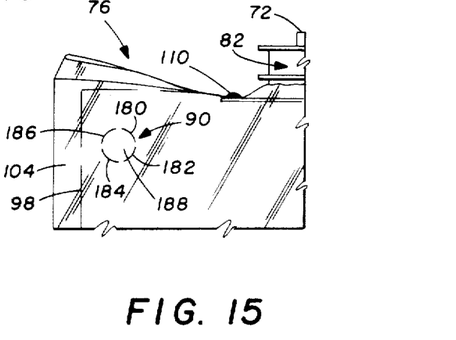
FIG. 15 illustrates another embodiment of the butterfly type valve with use with the flexible sack of the invention.

FIG. 15 illustrates another embodiment of the aperture valving invention. In this embodiment, the apertures are formed by four semicircular slits 180–186 to provide four small plastic hinges which support a flexible valve flap 188. Due to the molecular orientation of sheets of plastic, two of the four hinges defined by the slits 180–186 will be weaker than the remaining two hinges. Upon application of low vacuum to the system, the slits 180–186 provide a relatively small opening to ensure that the sack 76 is fully expanded for suction of medical fluid. However, under higher fluid flow, two of the small hinges formed by the slits 180–186 will rupture to provide a larger effective opening for increased flow rates through the aperture. Provision of the four slits 180–186 provides improved resistance control to the flap 188 during very low vacuum pressure application.

Figure 16:
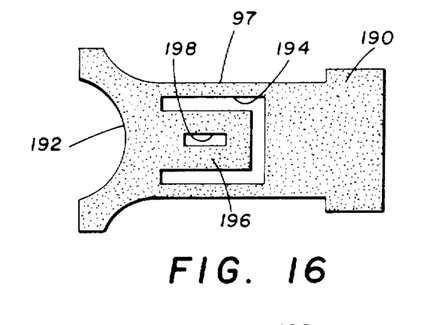
FIG. 16 is a top view of the float valve of the invention.

FIGS. 16–20 illustrate in detail the construction and operation of the float valve of the invention. FIG. 16 is a top view of the float valve 97 which comprises an elongated strip of flexible plastic material having low fluid absorption characteristics. The float valve includes a free end portion 190 which hangs below the vacuum inlet port during normal operating conditions and which obstructs the vacuum during overflow conditions. A generally curved cutout portion 192 is provided in the other end of the strip for abutting with the exterior of the projection 80 of the lid 64. A generally U-shaped cutout portion 194 defines a rectangular tab 196 which includes a slot 198 for receiving a pivot member depending from the underside of the lid 62. Rubber material which has been found to work well for the present float valve is a closed cell Neoprene rubber, manufactured and sold by B.F. Goodrich Company. Preferably, the material for constructing the float valve 97 comprises a cellular rubber or plastic material which has flexibility and low fluid absorption characteristics, but yet which has sufficient strength to obstruct the vacuum inlet during overflow conditions.

Figure 17:
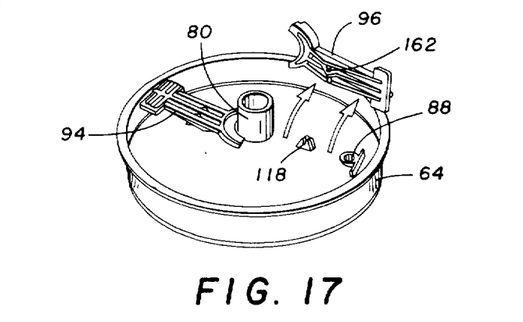
FIG. 17 illustrates the removal of the sack separator levers of the invention to enable application of the float valve shown in FIG. 16.

FIG. 17 illustrates how the sack separator lever 96 may be removed from the underside of the lid 64 by manually pulling the cylindrical projection 162 away from the pivot projection 118 which extends from the underside of the lid 64.

Figure 18:
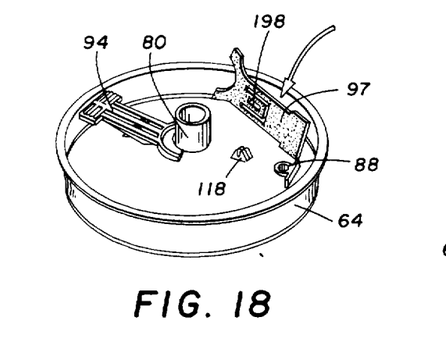
FIG. 18 illustrates the attachment of the present float valve to the underside of the container lid.
Figure 19:
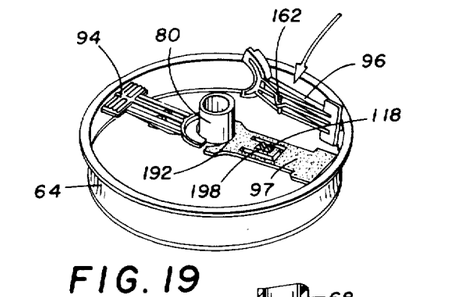
FIG. 19 illustrates the connection of the sack separator lever adjacent the float valve of the invention.

After removal of the lever 96, the float valve 97 is inserted over the pivot projection 118 as shown in FIG. 18. FIG. 18 illustrates how the slot 198 of the float valve 97 receives the pivot projection 118. FIG. 19 also illustrates how the curved end portion 192 abuts against the annular projection 80 to provide additional support to the inwardly directed end of the float valve 97. The U-shaped cutout portion 194 provides for greater flexibility of the float valve 97 while enabling the pivot projection 118 to be utilized both as a support for the float valve and as a pivot support for the lever 96. As shown in FIG. 19, after the float valve 97 is firmly attached to the pivot projection 118, the lever 96 is again snapped into pivotal connection with the projection 118. The float valve 97 is then firmly attached to the underside of lid 64.

Figure 20:
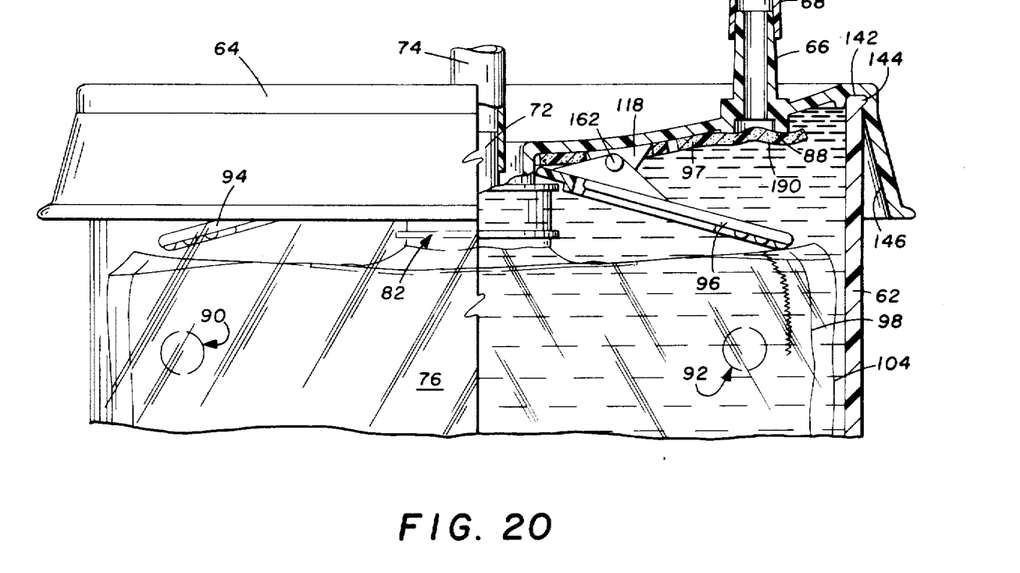
FIG. 20 is a partially sectioned view of the present container illustrating operation of the float valve during overflow conditions.

FIG. 20 illustrates the operation of the float valve 97 during overflow conditions. Under some operating conditions, excessive fluid may be introduced into the sack 76. When this occurs, the fluid first overflows from the inner sack 98 into the outer sack 104. If additional fluid is then directed into the sack 76, the fluid overflows into the aperture 90 into the interior of the container 62. When the level of fluid between the container 62 and the exterior of the sack 76 reaches the level of the float valve 97, the float valve 97 floats on the surface of the fluid and the free end 190 is carried upwardly by the fluid until the vacuum inlet orifice 88 is obstructed by the free end portion 190 as shown in FIG. 20. With the use of the proper types of flexible cellular material, the end portion 190 will be deformed upwardly into the vacuum inlet 88 and the air cells within the cellular material are compressed in order to provide a fluid tight obstruction to prevent fluid from being sucked into the vacuum system of the hospital. After an overflow condition occurs, the present float valve 97 may be snapped out of place and a fresh float valve installed as shown in FIGS. 17–19. The present float valve is extremely simple and economical to construct and manufacture and provides maintenance-free operation.

Figures 21, 22, 23, 24:
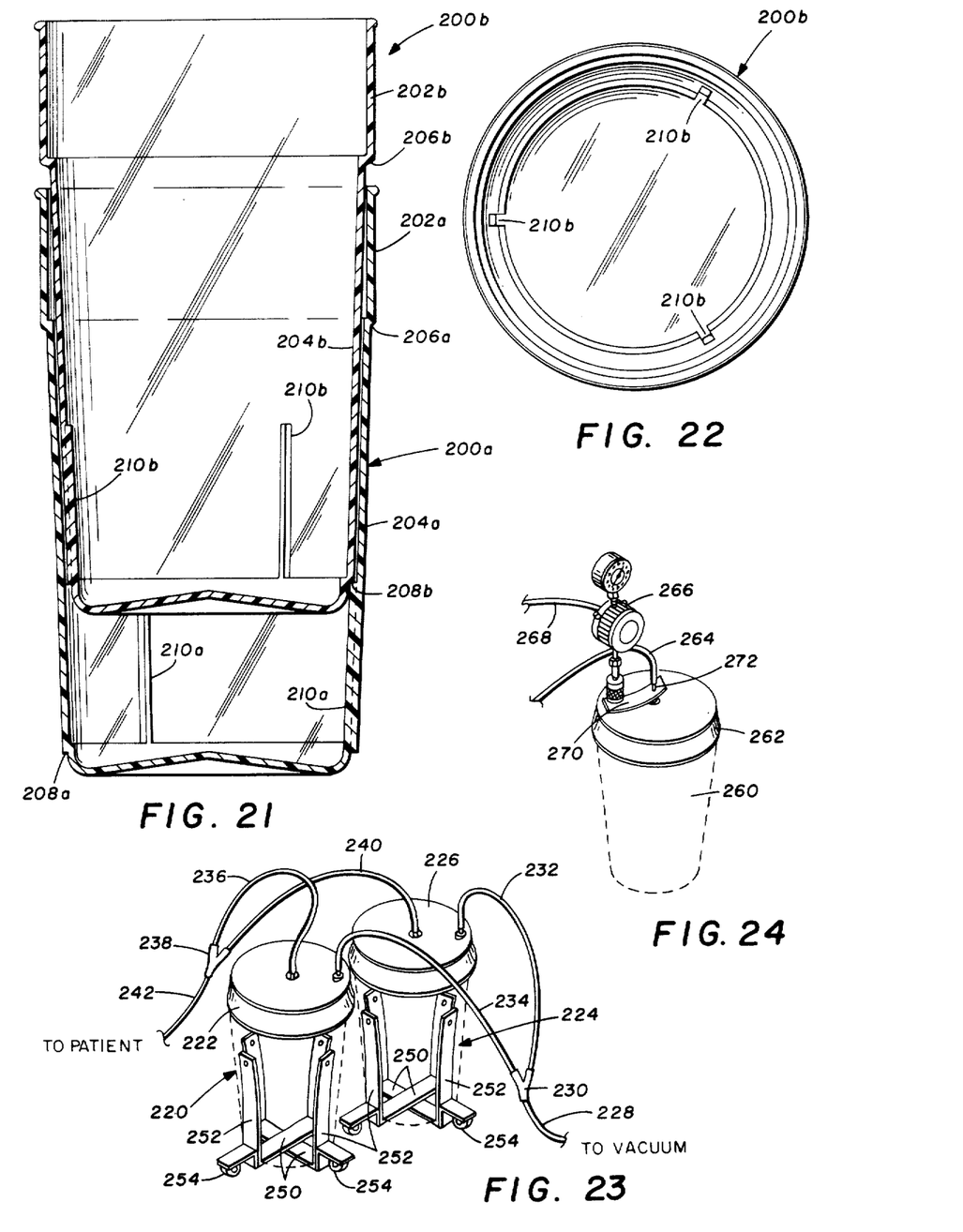
FIG. 21 illustrates the stacking of an embodiment of the fluid container.
FIG. 22 is a top view of the container of FIG. 21 illustrating the spaced apart stacking feet of the invention.
FIG. 23 illustrates a parallel connection for enabling two suction devices according to the invention to be simultaneously filed.
FIG. 24 illustrates the use of a conductive grounding strip according to the invention.

FIG. 21 illustrates another configuration of a container for use with the present invention which provides stacking for shipping and storage of the rigid container. As shown in FIG. 21, a first open-topped container 200a includes an upper cylindrical portion 202a which is joined with a lower frustoconical portion 204a by means of an annular shoulder 206a. Shoulder 206a may be utilized to support the container in an annular wall bracket. A second annular shoulder 208a is provided in the lower portion of the container for abutment with a lower container in a manner to be described. As shown in FIGS. 21 and 22, on the lower interior of the container 200a are 3 feet or projections 210a. The bottom of container 200a has an upwardly directed conical configuration.

A second container 200b is illustrated in a stacking configuration within container 200a. Container 200b is identical to container 200a and includes a cylindrical upper portion 202b, a shoulder 206b and a conical lower portion 204b. As shown in FIG. 21, the lower annular shoulder 208b of container 200b abuts with the top of the feet 210a to prevent the container 200b from being too tightly inserted within the container 200a. The length of the feet 210a is such that the shoulder 208b abuts with the top of the feet 210a prior to abutment of shoulder 206b with the top of container 200a. Container 200b also includes three feet or pedestals 210b to enable stacking of a third container in the manner illustrated.

FIG. 23 illustrates the interconnection of two of the present suction systems to enable parallel simultaneous filling of the two containers from a single patient area. A first container 220 includes a lid 222 which supports a flexible sack within the container in the manner previously described. A second suction container 224 includes a lid 226 which supports a second flexible sack within the container 224. A vacuum source is connected through a hose 228 to a Y-connection 230 for connection to a hose 232 which extends to a suction inlet lid 226. The Y-connection 230 is also connected to a second hose 234 which is connected to the suction inlet of lid 222. A hose 236 is connected to the fluid inlet port of the lid 222 and is connected to one end of a Y-connection 238. A second tube 240 is connected to the fluid inlet port of lid 226 and is connected to the other end of the Y-connection 238. A hose 242 extends from the Y-connection 238 to the patient area. Upon application of vacuum to hose 228, fluid is drawn from a patient area through tube 242 and tubes 236 and 240 into the flexible sacks within containers 220 and 224. The parallel connected system enables the system to be utilized for large operations and other instances when large fluid collection capacity is required.

FIG. 23 also illustrates the use of roll about supports for the fluid container of the invention. The support includes a lower generally X-shaped support 250 from which extend four upright members 252. The containers 220 and 224 are received between the upper members 252. Wheels 254 enable the supports to be freely rolled about an operating table or floor when desired.

Figure 25:
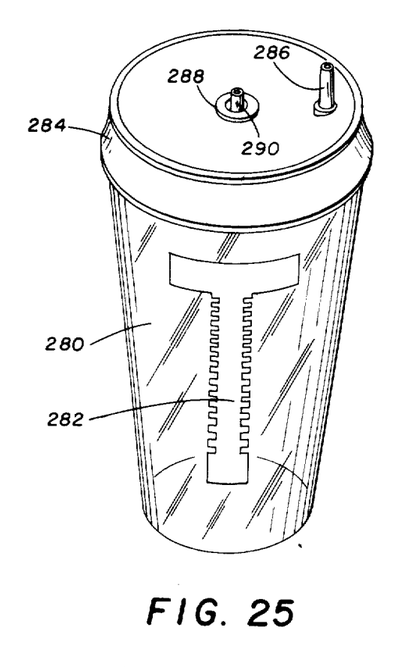
FIG. 25 illustrates the conversion of the present container into a disposable container.

FIG. 25 illustrates a conductive grounding strip for use with the invention. A container 260 includes a lid 262 constructed in accordance with the present invention. A tube 264 extends to a patient area and is connected to the fluid inlet port of the lid 262. A vacuum regulator 266 is connected to the vacuum inlet of the lid 262 and is connected through a tube 268 to a source of vacuum. The tubes 268 and 264 include conductive paths in order to prevent electric shock of the patient. However, if the tube 264 terminates in a plastic insulated lid, a path to ground will not be provided from the patient. Therefore, a black high carbon content rubber strip 270 is provided which includes an aperture 272 for receiving the end of the hose 264. The strip 270 includes an aperture at the other end thereof for receiving an end of the regulator 266. As the rubber strip 270 is conductive, tubing 264 is shorted to tubing 268 which is normally grounded. In this manner, a path to ground is provided from the patient to prevent sparks and the like from igniting the explosive oxygen atmosphere often present in operating rooms and the like.

FIG. 25 illustrates how the present container and lid may be modified to provide a disposable rigid medical fluid collecting system. The container 280 is constructed from transparent plastic in the same manner as the previously described container. A fluid level indicia 280 is printed upon the exterior of the container. A lid 284 is provided to cover the open top of the container 280. Lid 284 is constructed in the identical configuration as that previously described. A vacuum inlet port 286 is integrally formed in the lid 284 for connection to a source of reduced pressure.

Figure 26:
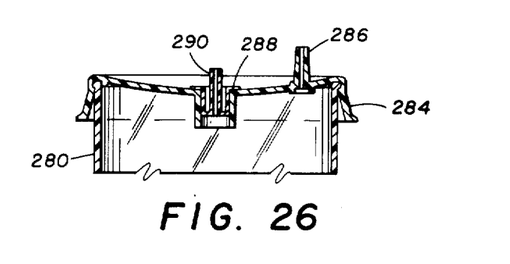
FIG. 26 is a sectional view of the top portion of the disposable container shown in FIG. 25.

In this embodiment, a plastic nipple 288 is rigidly fitted within the fluid inlet port of the lid 284. As shown in FIG. 26, the lid 284 is provided with a downwardly directed concavo-convex shape in the manner previously described. The plastic nipple is shaped in the same manner as the part 130 shown in FIG. 13 and includes an upper extending conduit 290 for connection to tubing which leads to a patient area. In this embodiment, the flexible sack of the invention is not required. Suction is merely applied to the vacuum inlet port 286 and fluid is drawn from the patient area through the conduit 290 into the container 280. Caps may be placed over the port 286 and the conduit 290 and the resulting closed system may then be completely disposed of if desired. In some cases, the container 280 may be cleaned and reutilized.

Figure 27:
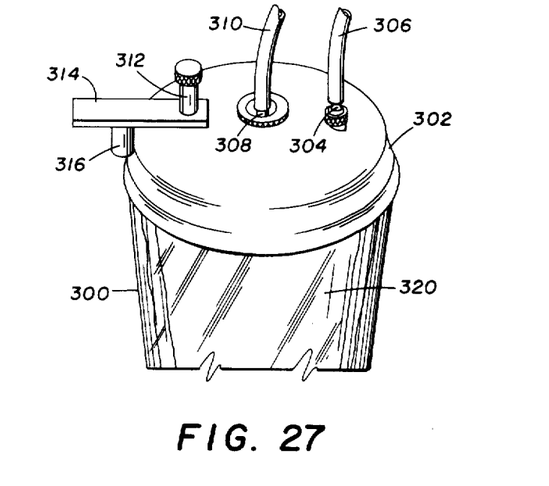
FIG. 27 is a perspective view of another embodiment of the present suction container assembly illustrating the use of a top mounted sack separator lever.
Figure 28:
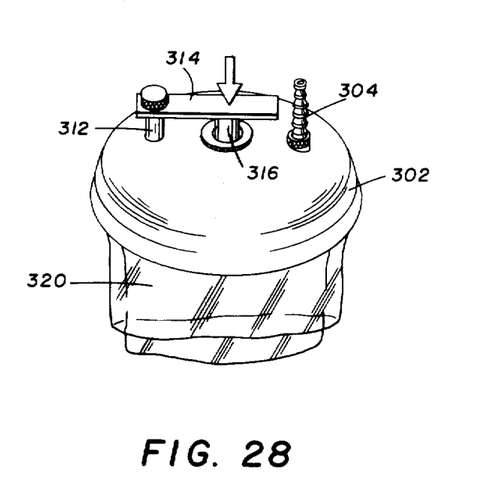
FIG. 28 illustrates the use of the sack separator lever shown in FIG. 27 to remove a sack from the container lid.
Figure 29:
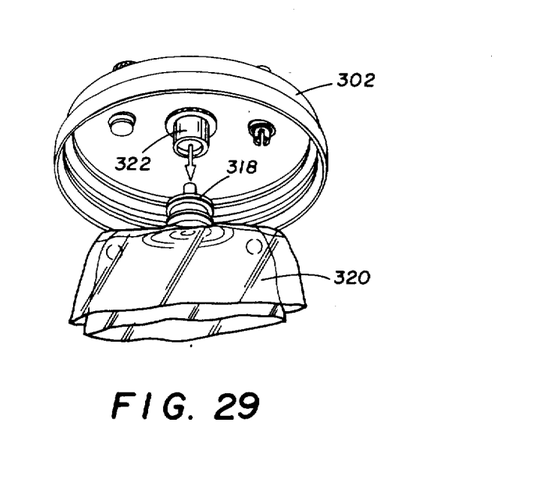
FIG. 29 illustrates the removal of the disposable sack from the underside of the container shown in FIGS. 27-28.

FIGS. 27–29 illustrate another embodiment of the present invention utilizing a different embodiment of a sack separating lever. FIG. 27 illustrates a rigid container 300 which threadedly receives a rigid plastic domed top 302. A vacuum inlet nipple 304 is attached to the top 302 and may be connected to a flexible hose 306 for connection to a source of reduced pressure. A fluid inlet conduit 308 is mounted in the top for connection to a hose 310 leading to a patient area to receive fluid. A post 312 is rigidly affixed to the top 302 and pivotally supports a rigid plate 314 having a cylindrical projection 316.

In use of the system shown in FIG. 27, a sack constructed in the previously described manner is connected beneath the lid 302. Vacuum is then applied through the hose 306 and fluid from the patient area is drawn through the tube 310 for collection within the collection sack within the container 300. When it is desired to separate the fluid filled sack from the container 300, the lid 302 is removed and the plate 314 is moved to the position shown in FIG. 28. The projection 316 is placed directly over the plastic port device 318 connected to the sack, and downward pressure is applied by the nurse or the operator. As shown in FIG. 29, the downward pressure causes the plastic port device 318 to the sack 320 to be disengaged from the annular downward projection 322 of the lid 302. In this manner, the sack 320 may be emptied and disposed of in the previously described manner. A new sack may then be inserted over the annular member projection 322 and the lid reattached to the container 300 for additional use of the system.

It may thus be seen that the present suction device may be very economically manufactured and utilized. Due to the flexible nature of the bags utilized, the suction apparatus may be conveniently stored in a relatively small package, thereby resulting in considerable space-saving in hospital environments. Because of the particular operation of the device, the flexible bags utilized are not subject to excessive stress during suction operation, and therefore may comprise relatively lightweight and economical plastic bags. The present device is extremely simple in design and construction, and thus is not generally subject to maintenance problems and may be operated with a minimum of instruction. Moreover, the bags of the present device do not tend to collapse in case of a vacuum leak in the cover or in the conduit members. The flexible bags of the invention are also completely disposable so that cross-contamination from patient to patient is reduced.

In addition, the present invention provides an improved medical suction device having a lid which is automatically attached to a container by application of vacuum thereto. The double lined flexible sack of the invention provides improved fluid integrity. The novel aperture valving structure of the invention enables the system to work with various degrees of suction. The float valve of the invention prevents fluid overflow from the system into the vacuum supply of a hospital. The sack separating levers of the invention enable a fluid filled sack to be easily disengaged from an upper lid without requiring a nurse to touch the fluid filled sack. Construction of the fluid inlet port device of the invention prevents the sack from being sucked off the lid during heavy application of pressure. The provision of the stacking feet in the lower interior of the container enables a plurality of the containers to be stacked together for ease in shipping and storage.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. In a medical suction assembly, the combination comprising:
    a fluid container having an annular bead extending around the upper portion thereof,
    a lid for said fluid container having a fluid inlet for communicating with a patient area and having a vacuum port for being connected to a source of vacuum,
    said lid including an annular groove on the underside thereof for sealingly receiving said bead to provide a vacuum tight seal for said container,
    an annular side wall extending from said annular groove and being outwardly flared to define a transient sealing portion below said groove for abutment with said annular bead of said container, said transient sealing portion providing a temporary vacuum seal upon the application of vacuum to said vacuum port sufficient to cause said lid to be pulled downwardly upon said container to seat said annular bead within said annular groove, and
    a float valve attached to said lid and including means movable in response to a predetermined level of fluid in said fluid container to obstruct said vacuum port to prevent fluid from being drawn through said vacuum port wherein said float valve comprises:
    an elongated strip of flexible material having low fluid absorption characteristics,
    a portion of said flexible strip being detachably connected to the underside of said lid, said strip having a free end which normally hangs below said vacuum port due to bending of said flexible strip when the fluid level within said container is below said predetermined level,
    said free end having sufficiently low fluid absorption characteristics to float on the fluid when the fluid reaches said predetermined level within said container to prevent the fluid from being drawn through said vacuum port.

2. The combination of claim 1 wherein said lid is constructed from flexible plastic and can be manually flexed to enable the removal thereof from said container.

3. The combination of claim 1 wherein the top of said lid has an inverted curved shape.

4. The combination of claim 1 and further comprising:
    means formed on the underside of said lid for supporting said float valve.

5. In a medical suction assembly, the combination comprising:
    a fluid canister,
    a lid for said fluid canister,
    said lid having a downwardly curved inverted top including a fluid inlet port in the central portion thereof and a vacuum port disposed in the peripheral area thereof,
    an annular edge portion extending downwardly from the periphery of said lid and being outwardly flared to provide finger space between the edge of said edge portion and said cansiter for applying, detaching and handling said lid, and
    a float valve attached to said lid and including means movable in response to a predetermined level of fluid in said canister to obstruct said vacuum port to prevent fluid from being drawn through said vacuum port wherein said float valve comprises:
    an elongated strip of flexible material having low fluid absorption characteristics,
    a portion of said flexible strip being detachably connected to the underside of said lid, said strip having a free end which normally hangs below said vacuum port due to bending of said flexible strip when the fluid level within said canister is below said predetermined level,
    said free end having sufficiently low fluid absorption characteristics to float on the fluid when the fluid reaches said predetermined level within said canister to prevent the fluid from being drawn through said vacuum port.

6. The combination of claim 5 wherein said lid has a generally uniform thin cross section and is flexible to enable snap on attachment and snap off detachment from said canister.

7. The combination of claim 5 and further comprising:
    an annular projection on the underside of said lid for frictionally supporting the upper portion of a flexible fluid collection sack.

8. In a medical suction assembly, the combination comprising:
    a fluid container,
    a lid for said fluid container,
    said lid including a fluid inlet port in the central portion thereof and a vacuum port disposed in the peripheral area thereof, and
    a float valve attached to the underside of said lid wherein said float valve comprises:
    an elongated strip of flexible material having low fluid absorption characteristics,
    a portion of said flexible strip being detachably connected to the underside of said lid, said strip having a free end which normally hangs below said vacuum port due to bending of said flexible strip when the fluid level within said canister is below said predetermined level, said free end having sufficiently low fluid absorption characteristics to float on the fluid when the fluid reaches said predetermined level within said canister to prevent the fluid from being drawn through said vacuum port.

9. The combination of claim 8 wherein said flexible strip has a generally curved end for abutting with the fluid inlet port downwardly projecting from the underside of said lid, a generally U-shaped cutout portion in said strip defining a tab extending toward said free end of said strip, said tab including an aperture for receiving a projection from the underside of said lid.

\* \* \* \* \*